United States Patent
Payne, Jr.

[11] Patent Number: 5,891,189
[45] Date of Patent: Apr. 6, 1999

[54] HEATING BAND DEVICE

[76] Inventor: Joe R. Payne, Jr., 320 22nd Ave. NE., Birmingham, Ala. 35215

[21] Appl. No.: 910,524

[22] Filed: Aug. 7, 1997

[51] Int. Cl.[6] ..................................................... A61F 5/02
[52] U.S. Cl. .......................... 607/108; 607/112; 219/212; 219/549; 601/15; 165/46
[58] Field of Search ............. 607/108–112, 148, 607/152; 602/19; 601/15, 49; 165/46; 219/212, 549

[56] References Cited

U.S. PATENT DOCUMENTS

| | | | |
|---|---|---|---|
| 4,279,255 | 7/1981 | Hoffman | 607/88 |
| 4,702,235 | 10/1987 | Hong | 607/108 X |
| 5,062,414 | 11/1991 | Grim | 607/108 X |
| 5,151,578 | 9/1992 | Phillips | 607/108 X |
| 5,378,225 | 1/1995 | Chatman, Jr. et al. | 607/108 X |

*Primary Examiner*—Jeffrey R. Jastrzab
*Assistant Examiner*—Ryan Carter

[57] ABSTRACT

A new heating band device for providing both heat and pressure to sore muscles and sprains. The inventive device includes an elongate elastomeric band member for wrapping around a body part and an elongate heating coil member embedded in a serpentine arrangement within the band member. A hook member secures the heating band device in place on the body part. A temperature control switch selectively controls the heat output of the heating coil member.

1 Claim, 2 Drawing Sheets

HEATING BAND DEVICE

BACKGROUND OF THE INVENTION

1. Field of the Invention

The present invention relates to body heating devices and more particularly pertains to a new heating band device for providing both heat and pressure to sore muscles and sprains.

2. Description of the Prior Art

The use of body heating devices is known in the prior art. More specifically, body heating devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art body heating devices include U.S. Pat. No. 4,042,803; U.S. Pat. No. 4,201,218; U.S. Pat. No. 4,695,703; U.S. Pat. No. 4,572,755; and U.S. Pat. No. 5,050,595.

While these devices fulfill their respective, particular objectives and requirements, the aforementioned patents do not disclose a new heating band device. The inventive device includes an elongate elastomeric band member for wrapping around a body part and an elongate heating coil member embedded in a serpentine arrangement within the band member. A hook member secures the heating band device in place on the body part. A temperature control switch selectively controls the heat output of the heating coil member.

In these respects, the heating band device according to the present invention substantially departs from the conventional concepts and designs of the prior art, and in so doing provides an apparatus primarily developed for the purpose of providing both heat and pressure to sore muscles and sprains.

SUMMARY OF THE INVENTION

In view of the foregoing disadvantages inherent in the known types of body heating devices now present in the prior art, the present invention provides a new heating band device construction wherein the same can be utilized for providing both heat and pressure to sore muscles and sprains.

The general purpose of the present invention, which will be described subsequently in greater detail, is to provide a new heating band device apparatus and method which has many of the advantages of the body heating devices mentioned heretofore and many novel features that result in a new heating band device which is not anticipated, rendered obvious, suggested, or even implied by any of the prior art body heating devices, either alone or in any combination thereof.

To attain this, the present invention generally comprises an elongate elastomeric band member for wrapping around a body part and an elongate heating coil member embedded in a serpentine arrangement within the band member. A hook member secures the heating band device in place on the body part. A temperature control switch selectively controls the heat output of the heating coil member.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature an essence of the technical disclosure of the application. The abstract is neither intended to define the invention of the application, which is measured by the claims, nor is it intended to be limiting as to the scope of the invention in any way.

It is therefore an object of the present invention to provide a new heating band device apparatus and method which has many of the advantages of the body heating devices mentioned heretofore and many novel features that result in a new heating band device which is not anticipated, rendered obvious, suggested, or even implied by any of the prior art body heating devices, either alone or in any combination thereof.

It is another object of the present invention to provide a new heating band device which may be easily and efficiently manufactured and marketed.

It is a further object of the present invention to provide a new heating band device which is of a durable and reliable construction.

An even further object of the present invention is to provide a new heating band device which is susceptible of a low cost of manufacture with regard to both materials and labor, and which accordingly is then susceptible of low prices of sale to the consuming public, thereby making such heating band device economically available to the buying public.

Still yet another object of the present invention is to provide a new heating band device which provides in the apparatuses and methods of the prior art some of the advantages thereof, while simultaneously overcoming some of the disadvantages normally associated therewith.

Still another object of the present invention is to provide a new heating band device for providing both heat and pressure to sore muscles and sprains.

Yet another object of the present invention is to provide a new heating band device which includes an elongate elastomeric band member for wrapping around a body part and an elongate heating coil member embedded in a serpentine arrangement within the band member. A hook member secures the heating band device in place on the body part. A temperature control switch selectively controls the heat output of the heating coil member.

Still yet another object of the present invention is to provide a new heating band device that provides the benefits of both a heating pad and an elastic wrap in one device.

Even still another object of the present invention is to provide a new heating band device that may be wrapped tightly around an injured body part, concentrating heat in a particular area.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
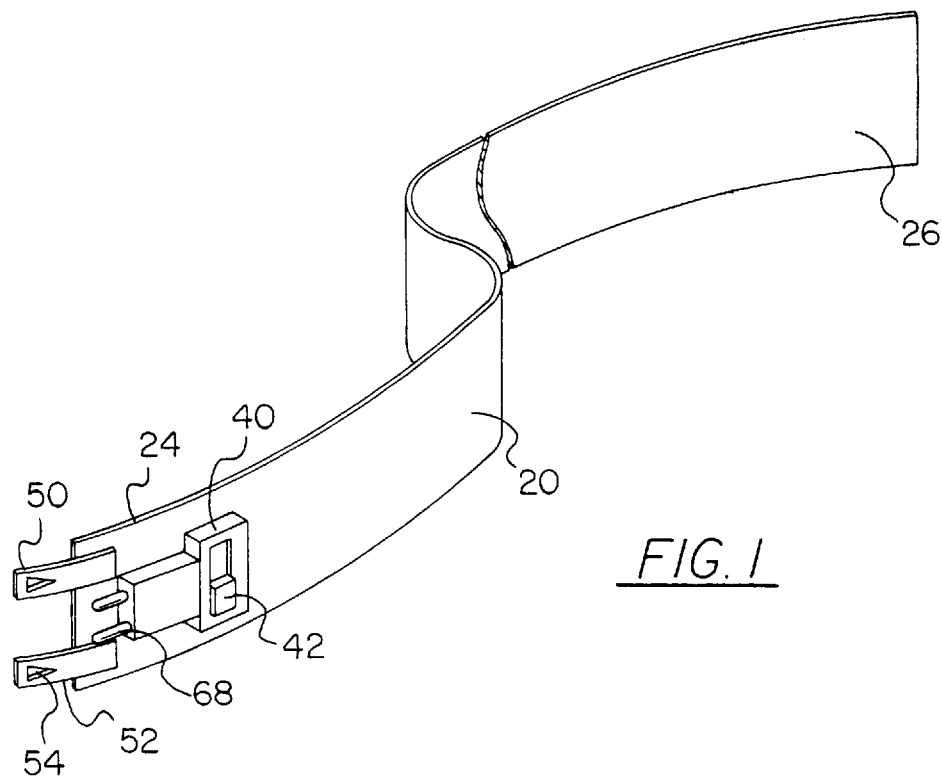
FIG. 1 is a perspective view of a new heating band device according to the present invention.

With reference now to the drawings, and in particular to FIGS. 1 through 4 thereof, a new heating band device embodying the principles and concepts of the present invention and generally designated by the reference numeral 10 will be described.

As best illustrated in FIGS. 1 through 4, the heating band device 10 generally comprises an elongate elastomeric band member 20 for wrapping around a body part and an elongate heating coil member 30 serpentinely embedded within the band member 20. An attachment means 50 secures the heating band device 10 in place on the body part. A temperature adjustment means 40 selectively controls the heat output of the heating coil member 30 and a power source 60 provides energy to the heating coil member 30.

The elongate elastomeric band member 20 is designed to be stretched along its longitudinal axis and flexible throughout its entirety. Ideally, the stretchability and flexibility of the band member 20 is similar to that of an elastic medical wrap, such as the type commonly used for sprains.

The attachment means 50 is designed to attach the band member first end 24 to a portion of the band member 20. Preferably, as shown in FIG. 1, the attachment means 50 includes a hook member 52 that is coupled to the first end 24 of the band member 20. The hook member 54 has a hook portion 56 that detachably attaches to the material of the band member 20. Ideally, the hook member 54 is similar to the type of fasteners used on elastic medical wraps. Although the use of Velcro as a fastener is acceptable, the use of a hook-type fastener is preferable to the use of Velcro because Velcro would limit the flexibility of the band member 20. Ideally, the band member 20 is designed to be as flexible as an elastic medical bandage to maximize the versatility of the heating band device 10.

The heating coil member 30 provides heat for the heating band device 10. The heating coil member 30 is embedded within the interior 22 of the band member 20 and extends from the band member first end 24 to the band member second end 26.

Figure 2:
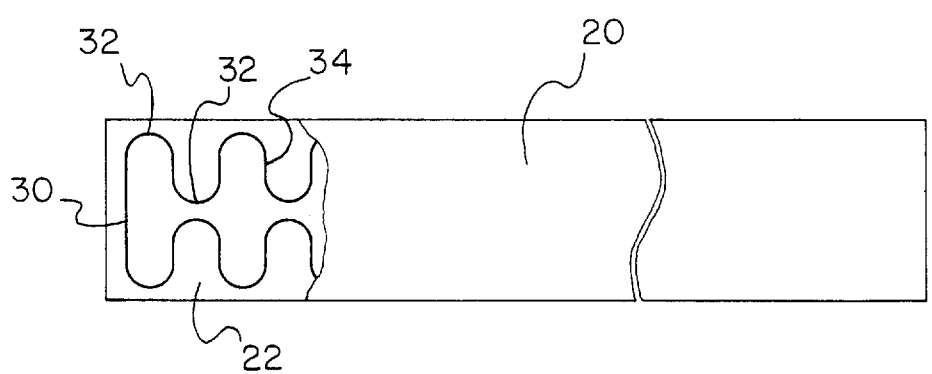
FIG. 2 is a partial breakaway view of the present invention illustrating the serpentine arrangement of the heating coil member.

The heating coil member 30 is designed to stretch with the band member 20 without breaking. To achieve this, the heating coil member 30 includes a plurality of alternating curved portions 32 and straight portions 34. As shown in FIG. 2, the curved and straight portions 32, 34 are arranged in a serpentine arrangement along the band member longitudinal axis. The straight portions 34 are aligned substantially transversally to the band member longitudinal axis.

Because the heating coil member 30 may stretch with the band member 20, the heating band device 10 provides the benefits of both a heating pad and an elastic wrap in one device. Furthermore, such a design allows the heating band device 10 to be wrapped tightly around an injured body part, concentrating the heat in that particular area.

Figure 3:
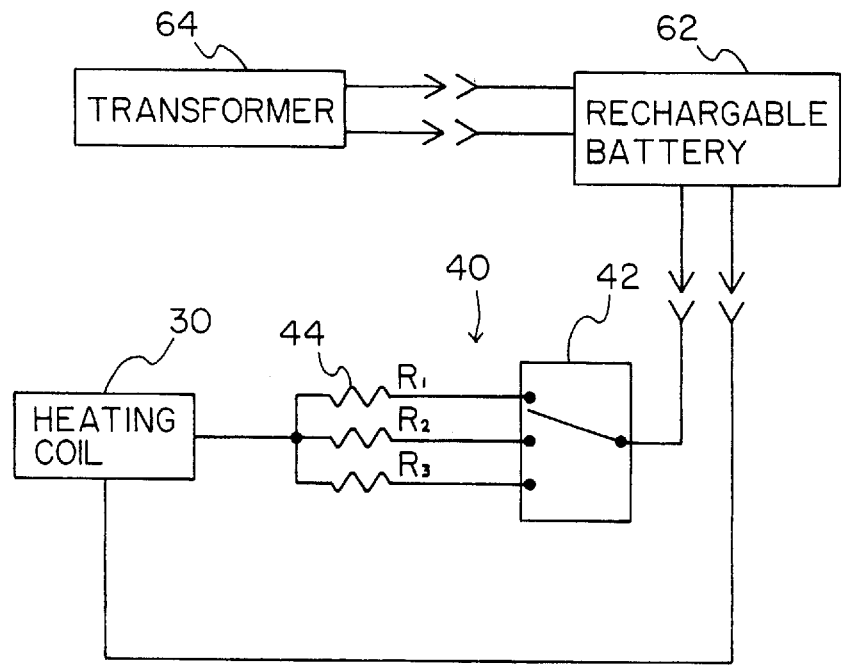
FIG. 3 is a circuit diagram of the present invention.

FIG. 3 provides an example of the circuitry of the heating band device 10. The temperature adjustment means 40 permits selective adjustment of the amount of heat provided by the heating coil member 30. Preferably, as illustrated in FIG. 3, a temperature control switch 42 directs the electric current passing between the power source 60 and the heating coil member 30 through a plurality of resistors 44.

Figure 4:
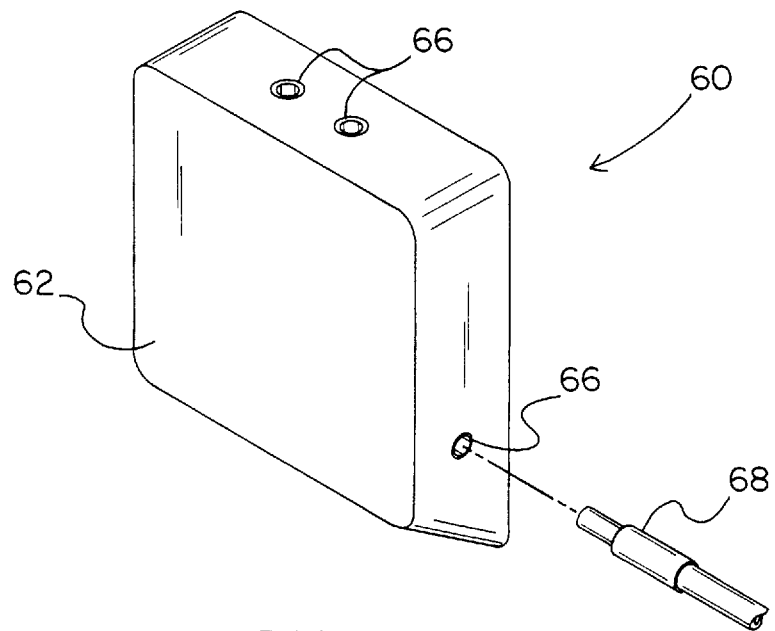
FIG. 4 is a perspective view of a detachable rechargeable battery the present invention.

The power source 60 is operatively coupled to the heating coil member 30 to provide energy to the heating coil member 30. Ideally, the power source 60 includes a battery 62 that may be rechargeable. A rechargeable battery may be recharged by a releasably attached recharging unit (not shown) including a transformer 64. Even more ideally, the battery 62 is detachable. FIG. 4 shows a detachable, rechargeable battery 62 including a pair of sockets 66 into which heating band device electrical plugs 68 are inserted and a socket 66 into which an electrical plug 68 that extends from the recharging unit is inserted.

Optionally, the power source 60 includes a housing for a battery (not shown). Also optionally, the power source 60 includes a power unit (not shown) removably coupled to the heating band device 10 and including a transformer 64.

The heating band device 10 is used to provide heat to sore muscles and sprained body parts. In use, the band member 20 of the heating band device 10 is wrapped tightly around a body part such as an ankle, allowing the band member 20 to stretch around the body part in the same manner as an elastic medical wrap. The band member first end 24 is then attached to a portion of the band member 20 by the attachment means 50 to hold the heating band device 10 in place. The power source 60 is connected and activated. A suitable temperature is selected by manipulating the temperature adjustment means 40.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A heating band device for wrapping around a portion of a body, comprising:

an elongate elastomeric band member having an interior, a first end, a second end and a longitudinal axis, said band member being stretchable along said longitudinal axis;

an elongate heating coil member for providing heat, said heating coil member having a plurality of alternating curved portions and straight portions, wherein the curved portions each define an upper row having a plurality of interconnected inverted U-shaped shaped sections and a lower row adjacent to and spaced below the upper row and having a plurality of interconnected U-shaped sections, said heating coil member being embedded within said band member interior, said heating coil being extended along said band member longitudinal axis between said band member first end and said band member second end;

a temperature adjustment means for selectively adjusting the temperature of the heat provided by said heating coil member, the temperature adjustment means including a vertically oriented slider switch mounted to an outer surface of an end of the band member;

an attachment means for attaching said band member first end to a portion of said band member, wherein said attachment means includes a hook member having a hook portion, said hook member being coupled to a said band member end, said hook member hook portion being for detachable attachment to a portion of said band member;

a pair of electrical plugs being electrically coupled to said heating coil, the plugs fixedly mounted adjacent to the switch of the temperature adjustment means and extending toward the end of the band member in a horizontally oriented, parallel manner;

a power source being operatively coupled to said heating coil, said power source being for providing energy to said heating coil member for providing heat therefrom;

wherein said power source includes a detachable rechargeable battery, said battery having a pair of sockets, wherein said electrical plugs are removably insertable into said sockets of said battery such that the battery is fixed with respect to the band member;

a releasably attached recharging unit, said recharging unit having an electrical plug for attaching to said battery;

wherein said battery further includes a socket for receiving said electrical plug of said recharging unit; and wherein said heating coil member curved portions and said heating coil member straight portions are arranged in a serpentine arrangement along the band member longitudinal axis to permit extension of said heating coil member in correspondence with stretching of said band member along said band member longitudinal axis, said heating coil member straight portions being aligned substantially transversally to said band member longitudinal axis.

* * * * *